United States Patent
Hirszowicz et al.

(10) Patent No.: US 7,824,370 B2
(45) Date of Patent: Nov. 2, 2010

(54) CATHETER

(75) Inventors: Eran Hirszowicz, Ramat Gan (IL); Orit Hirszowicz, Ramat Gan (IL); Yoav Turgeman, Kfar Tavor (IL); Omri Mairon, Zichron Ya'acov (IL)

(73) Assignee: Angioslide Limited, Herzliya (IL)

( * ) Notice: Subject to any disclaimer, the term of this patent is extended or adjusted under 35 U.S.C. 154(b) by 373 days.

(21) Appl. No.: 11/587,179

(22) PCT Filed: Apr. 21, 2005

(86) PCT No.: PCT/IL2005/000420

§ 371 (c)(1),
(2), (4) Date: Nov. 5, 2007

(87) PCT Pub. No.: WO2005/102184

PCT Pub. Date: Nov. 3, 2005

(65) Prior Publication Data

US 2008/0051706 A1 Feb. 28, 2008

(30) Foreign Application Priority Data

Apr. 22, 2004 (IL) .................. 161554

(51) Int. Cl.
*A61M 31/00* (2006.01)
(52) U.S. Cl. ............... 604/103.03; 604/96.01
(58) Field of Classification Search . 604/96.01–103.14, 604/104–109; 606/192, 194, 200
See application file for complete search history.

(56) References Cited

U.S. PATENT DOCUMENTS

| | | | |
|---|---|---|---|
| 4,469,100 A * | 9/1984 | Hardwick | 606/127 |
| 4,748,982 A | 6/1988 | Horzewski et al. | |
| 4,762,129 A | 8/1988 | Bonzel | |
| 5,254,091 A * | 10/1993 | Aliahmad et al. | 604/103.06 |
| 5,307,814 A * | 5/1994 | Kressel et al. | 600/423 |
| 5,785,675 A | 7/1998 | Drasler et al. | |
| 6,039,721 A * | 3/2000 | Johnson et al. | 604/508 |
| 6,695,810 B2 | 2/2004 | Peacock, III et al. | |
| 7,201,770 B2 * | 4/2007 | Johnson et al. | 623/1.12 |
| 2002/0177870 A1* | 11/2002 | Sepetka et al. | 606/194 |
| 2003/0105508 A1* | 6/2003 | Johnson et al. | 623/1.11 |

(Continued)

FOREIGN PATENT DOCUMENTS

EP 359 489 3/1990

(Continued)

OTHER PUBLICATIONS

International Search Report for PCT/IL2005/000420 mailed Jul. 29, 2005.

*Primary Examiner*—Nicholas D Lucchesi
*Assistant Examiner*—Gerald Landry, II
(74) *Attorney, Agent, or Firm*—Nixon & Vanderhye P.C.

(57) ABSTRACT

A system comprising a catheter (12) having an expandable element (18), which when expanded, has an annular shape surrounding a passageway. The expandable element in the expanded state is rollable along at least a portion of the shaft of the catheter without slipping. The system may be used for delivering an object to a site in the body, retrieving an object from a body, removing debris and/or other particulate matter from a blood vessel, and distending and/or expanding a pathologically-involved region of a blood vessel wall.

12 Claims, 8 Drawing Sheets

U.S. PATENT DOCUMENTS

| | | |
|---|---|---|
| 2003/0130672 A1 | 7/2003 | Dobrava et al. |
| 2005/0004553 A1 | 1/2005 | Douk |
| 2005/0154414 A1 | 7/2005 | Perreault et al. |

FOREIGN PATENT DOCUMENTS

| | | |
|---|---|---|
| EP | 380873 | 5/1994 |
| EP | 1333778 | 11/2001 |
| GB | 2054385 | 2/1981 |
| WO | WO 84/01513 | 4/1984 |
| WO | WO 0038776 | 7/1988 |
| WO | 02/38084 | 5/2002 |
| WO | 2005/041788 A | 5/2005 |

* cited by examiner

CATHETER

PCT/IL2005/000420 filed 21 Apr. 2005, which designated the U.S. and claimed priority of IL 161554 filed 22 Apr. 2004, the entire contents of each of which are hereby incorporated by reference.

FIELD OF THE INVENTION

The present invention relates to invasive medical devices, and more specifically to such devices for the delivery and retrieval of objects in the body.

BACKGROUND OF THE INVENTION

Catheters are medical devices that are used to deliver or retrieve objects in the body. The catheter tip is inserted into the body through a natural or artificial opening and delivered to a desired location. For example, a catheter is used to deliver and deploy a stent in an arterial stenosis. Endoscopic catheters are used to deliver an imaging device for gastrointestinal use.

U.S. Pat. No. 5,437,638 to Bowman discloses a multilumen catheter having a plurality of inflatable tubes at its tip. Each tube is attached to a different lumen, so that each tube may be individually inflated and deflated. The tubes are initially inserted into their respective lumens. In a procedure to open a constricted body passage, the tubes are inflated in the constriction. The tubes may also be provided with gripping surfaces and are manipulated by appropriate fluid pressures to grasp and recover objects in a body passageway.

U.S. Pat. No. 5,941,895 to Myler et al discloses a catheter for the retrieval of a stent. The catheter includes a tubular body and an axially moveable guidewire that are adapted to grasp engagement members on a stent to be retrieved.

U.S. Pat. No. 5,109,830 to Cho discloses a catheter having a tip designed to facilitate navigation of the catheter through the cardiovascular system. The tip has an inner element having a memorized preformed curved shape that it assumes when it is not disposed within an outer restraining sleeve. When in the sleeve, the inner element is straightened by the rigidity of the sleeve. The inner element is removed from the sleeve in order to facilitate navigation of the tip around a curve or bend in a blood vessel. The inner element is disposed in the sleeve when passing through a straight region of a blood vessel.

U.S. Pat. No. 4,597,389 to Ibrahim discloses a catheter having an annular balloon at its tip for grasping an object. The catheter tip is delivered to the object to be grasped with the balloon in its deflated state. The balloon is then positioned with the object in the central passageway of the annular balloon. As the balloon is inflated, the central passageway becomes constricted so as to grasp the object. The catheter is then withdrawn from the body.

SUMMARY OF THE INVENTION

The present invention provides a system comprising a catheter and an expandable element. The expandable element may be for example, an inflatable balloon. In its expanded state, the expandable element has an annular shape surrounding a central passageway. The expandable element is configured to roll on the catheter shaft without slipping when at least a portion of the shaft is in the passageway. The expandable element is mounted on the catheter shaft and is delivered to a body site in an unexpanded state. The expandable element is then brought to the expanded state. As described in detail below, the catheter may be used to deliver or retrieve an object into or from a body passageway. The catheter may also be used to retrieve atheromatous plaque debris and other particulate, solid or semi-solid matter present in pathologically-involved blood vessels, and to remove said matter from the body. The system may also be used to assist in navigating the catheter tip in narrow or curved body passages.

Thus, in its first aspect, the invention provides a system comprising:
  (a) a catheter having a shaft; and
  (b) an expandable element, the expandable element having an expanded state and having an annular shape surrounding a passageway in the expanded state,
    wherein the catheter and expandable element are configured so that the expandable element in the expanded state is rollable along at least a portion of the shaft without slipping when a portion of the shaft is positioned in the passageway.

In its second aspect, the invention provides a method for delivering an object to a site in the body, comprising:
  (a) mounting the object onto a catheter, the catheter comprising a shaft and an expandable element, the expandable element having an expanded state and having in the expanded state an annular shape surrounding a passageway, wherein the catheter and expandable element are configured so that the expandable element in the expanded state is rollable along at least a portion of the shaft without slipping when a portion of the shaft is positioned in the passageway;
  (b) delivering the object on the catheter to the body site;
  (c) bringing the expandable element into the expanded state so that the expandable element presses upon one or more body structures; and
  (d) moving the shaft anteriorly so as to cause the expandable element to roll posteriorly on the shaft without slipping.

In its third aspect, the invention provides a method for retrieving an object from a body site comprising:
  (a) delivering a catheter to the body site, the catheter comprising:
    (aa) a shaft;
    (ab) an expandable element, the expandable element having an expanded state and having in the expanded state an annular shape surrounding a passageway, wherein the catheter and expandable element are configured so that the expandable element in the expanded state is rollable along at least a portion of the shaft without slipping when a portion of the shaft is positioned in the passageway; and optionally further comprising
    (ac) a ramming mechanism that is capable of rolling the expandable element anteriorly on the shaft;
  (b) bringing the expandable element into the expanded state;
  (c) rolling the expandable element in the expanded state anteriorly so as to roll over the object thereby bringing the object into the passageway;
  (d) removing the catheter from the body.

In its fourth aspect, the invention provides a method for removing debris and/or other particulate matter from a blood vessel comprising:
  (a) delivering a catheter system via the peripheral vasculature to a pathologically-involved region of said blood vessel, wherein said catheter system comprises:
    i) a shaft
    ii) an expandable element, the expandable element having an expanded state and having in the expanded state an annular shape surrounding a passageway, wherein the catheter and expandable element are configured so that the expandable element in the expanded state is rollable along at least a portion of the shaft without slipping when a portion of the shaft is positioned in the passageway;
(b) bringing the expandable element into the expanded state;
(c) rolling the expandable element in the expanded state posteriorly or anteriorly or both so as to roll over the object thereby bringing said debris and/or other particulate matter into said passageway;
(d) deflating said expandable element, thereby entrapping said debris and/or other particulate matter between the deflated expandable element and the catheter shaft;
(e) removing the catheter system together with the entrapped debris and/or other particulate matter from the body by means of withdrawing said catheter system through the vasculature.

In its fifth aspect, the invention provides method for distending and/or expanding a pathologically-involved region of a blood vessel wall and removing debris and/or other particulate matter from said blood vessel comprising:
(a) delivering a catheter system via the peripheral vasculature to a location distal to the pathologically-involved region, wherein said catheter system comprises:
  i) a shaft
  ii) an expandable element, the expandable element having an expanded state and having in the expanded state an annular shape surrounding a passageway, wherein the catheter and expandable element are configured so that the expandable element in the expanded state is rollable along at least a portion of the shaft without slipping when a portion of the shaft is positioned in the passageway;
(b) bringing the expandable element into the expanded state;
(c) rolling the expandable element in the expanded state proximally or distally or both so as to roll over the object thereby bringing said debris and/or other particulate matter into said passageway and expanding the blood vessel wall by a squeezing or rolling mechanism;
(d) deflating said expandable element, thereby entrapping said debris and/or other particulate matter between the deflated expandable element and the catheter shaft;
(e) removing the catheter system together with the entrapped debris and/or other particulate matter from the body by means of withdrawing said catheter system through the vasculature.

In its sixth aspect, the invention provides a method for distending and/or expanding a pathologically-involved region of a blood vessel wall and removing debris and/or other particulate matter from said blood vessel comprising:
(a) delivering a catheter system via the peripheral vasculature to a location proximal to the pathologically-involved region, wherein said catheter system comprises:
  i) a shaft
  ii) an expandable element, the expandable element having an expanded state and having in the expanded state an annular shape surrounding a passageway, wherein the catheter and expandable element are configured so that the expandable element in the expanded state is rollable along at least a portion of the shaft without slipping when a portion of the shaft is positioned in the passageway;
(b) bringing the expandable element into the expanded state;
(c) rolling the expandable element in the expanded state proximally or distally or both so as to roll over the object thereby bringing said debris and/or other particulate matter into said passageway and expanding the blood vessel wall by a squeezing or rolling mechanism;
(d) deflating said expandable element, thereby entrapping said debris and/or other particulate matter between the deflated expandable element and the catheter shaft;

removing the catheter system together with the entrapped debris and/or other particulate matter from the body by means of withdrawing said catheter system through the vasculature.

In its seventh aspect, the invention provides a balloon bearing a sleeve on its outer surface, wherein a portion of the inner surface of the wall of said sleeve is attached at one or more attachment points to the outer surface of said balloon, such that an annular space exists between said sleeve and at least a portion of the outer surface of said balloon on at least one side of said attachment points.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 11 illustrates an embodiment of the catheter system of the present invention in which an expandable stent is mounted on the external surface of a balloon.

DETAILED DESCRIPTION OF THE INVENTION

Figure 1:
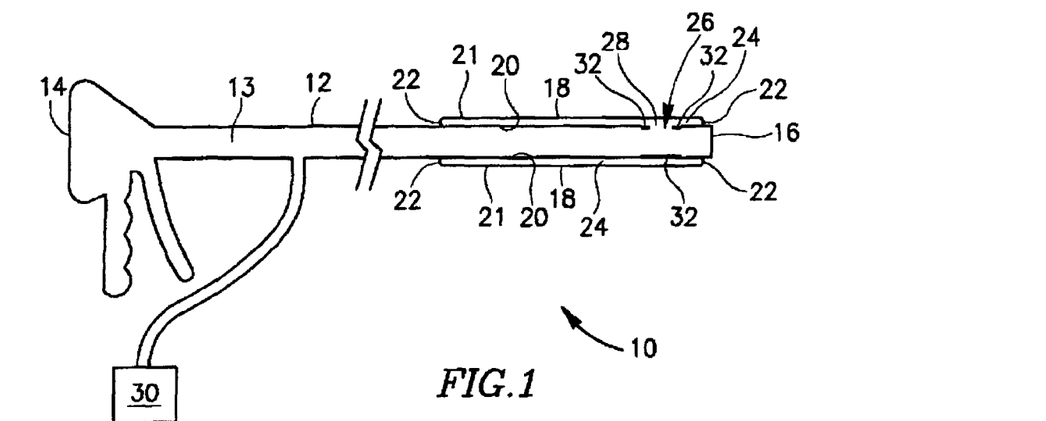
FIG. 1 shows a system in accordance with one embodiment of the invention.

FIG. 1 shows a catheter 10 in accordance with one embodiment of the invention. The catheter 10 has a cylindrical shaft 12 extending from its proximal end 14 to its distal end 16. The cylindrical shaft 12 may have a single lumen 13, as shown in FIG. 1, or it may have two or more lumens (not shown). In accordance with the invention, at the distal end 16 is an expandable element 18. The expandable element 18 may be an inflatable balloon 18, as shown in FIG. 1. This is by way of example only, and other types of expandable elements are contemplated within the scope of the invention. For example, the expandable element may be resiliently compressible element that is maintained in a compressed state by means of a restraining sleeve that is removed in order to allow the element to attain its expanded state. Alternatively, the expandable element may be a recovery coil, a self-expendable element, or an element formed from a shape-memory material or other means. The balloon 18 is shown in FIG. 1 in its deflated state. In this state the balloon is a cylindrical shell formed from an inner layer 20 and an outer layer 21. The inner and outer layers 20 and 21 are formed from a biocompatible flexible fluid impervious material. Materials for the manufacture of balloons for use in invasive medical devices are known in the art and include polyolefines (such as polyethylene, polypropylene and polypentene), polyesters (such as Mylar), polyurethane, polyamides (nylons), polyamines, polyvinyls (such as flexible polyvinylchloride, or PVA), liquid crystal polymers, styrene polymers (such as ABS) and other polymers such as silicone, latex, thermoplastic elastomers, polyethylene terephthalates, polyacrylenesulfide, polycarbonate, polysulfone, polyimide, polyeterimide, Peek; as well as copolymers, poly-blends and transformed species (e.g. following irradiation, cross linking or chemical treatment) of the aforementioned materials or of other materials, providing they have the appropriate biomechanical properties.

The inner and outer layers 20 and 21 are continuous with each other. For example, the inner and outer layers 20 and 21 may be welded together at circular seams 22. The balloon thus has an annular lumen 24. The lumen 24 is collapsed when the balloon 18 is in its deflated state shown in FIG. 1. The lumen 24 is in fluid communication with the lumen of the catheter shaft through an opening 26 in the wall of the shaft, and an overlying opening 28 in the inner layer 20.

The balloon having an annular lumen (as described hereinabove) is attached to the catheter shaft at one or more points on the inner circumference of the balloon. At one or more of these attachment points there is an opening in the balloon that is situated such that it overlays a similarly-sized and shaped opening in the shaft wall, thereby permitting the passage of an inflation medium between the lumen of the catheter shaft and the internal space of the balloon. The number of attachment points is not limited and these points can be arranged in any suitable or convenient arrangement, for example including (but not limited to) longitudinal, circumferential, helical or other arrangements.

Figure 7:
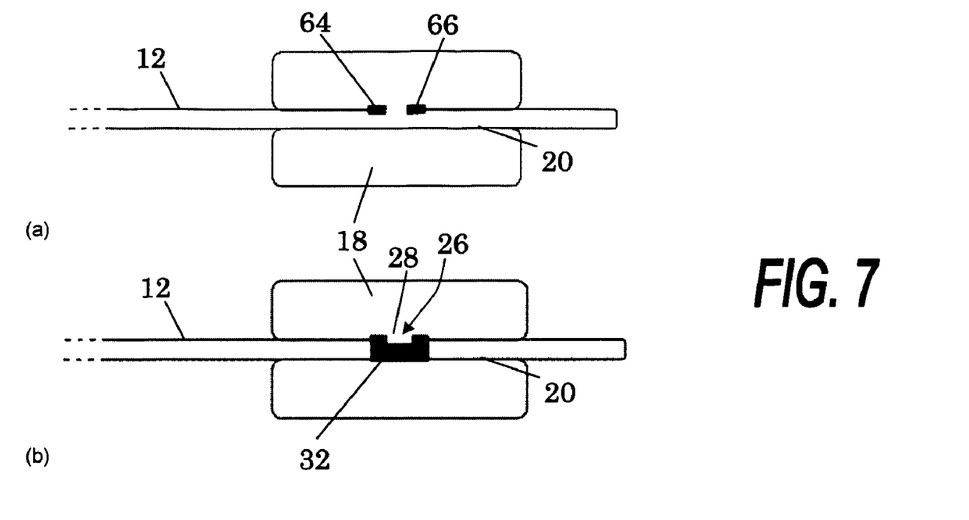
FIG. 7 illustrates two different modes of attachment of the balloon to the catheter shaft: point attachment (illustration a) and circumferential attachment (illustration b)

In one preferred embodiment of the present invention (as depicted in FIG. 7a), the inner layer 20 is attached to the outer surface of the catheter shaft 12 at two discrete attachment regions 64 and 66. In another embodiment of the present invention (as shown in FIG. 7b), the inner layer 20 is bonded to the catheter shaft in a single circular band 32 around the shaft 12 that surrounds catheter opening 26 and balloon opening 28. In a particularly preferred embodiment, the balloon inner layer 20 is attached to the catheter shaft (either at two discrete regions or as a single circular band, as described in the two immediately preceding preferred embodiments and shown in FIGS. 7a and 7b) as close as possible to the margins of shaft opening 26, such that, in the case of the embodiment depicted in FIG. 7a, the distance between the distal side of attachment region 64 and the proximal side of attachment region 66 approximates to the diameter of opening 26. In the case of the particularly preferred embodiment when used with a circular band attachment (as shown in FIG. 7b), the width of said circular band (i.e. the distance between the proximal and distal margins of said band) is kept as small as possible in order to maximize the length of the catheter shaft over which the balloon is able to roll. Regardless of which specific attachment geometry is used, the bonding of the balloon to the catheter shaft at the attachment site(s) may be achieved by the use of any suitable biocompatible adhesive, heat welding, ultrasonic welding, or mechanical means.

Referring again to FIG. 1, the balloon 18 is inflated by delivering a fluid such as compressed air, carbon dioxide, contrast media or water from a source 30 through the lumen 13 of the catheter shaft to the lumen of the balloon 18.

Figure 2A:
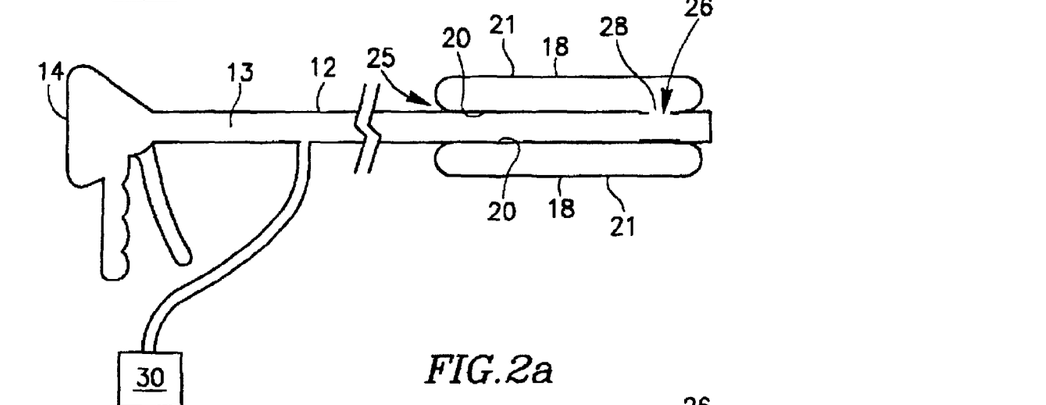
FIG. 2 shows the system of FIG. 1 after inflation of the balloon.
Figure 2B:
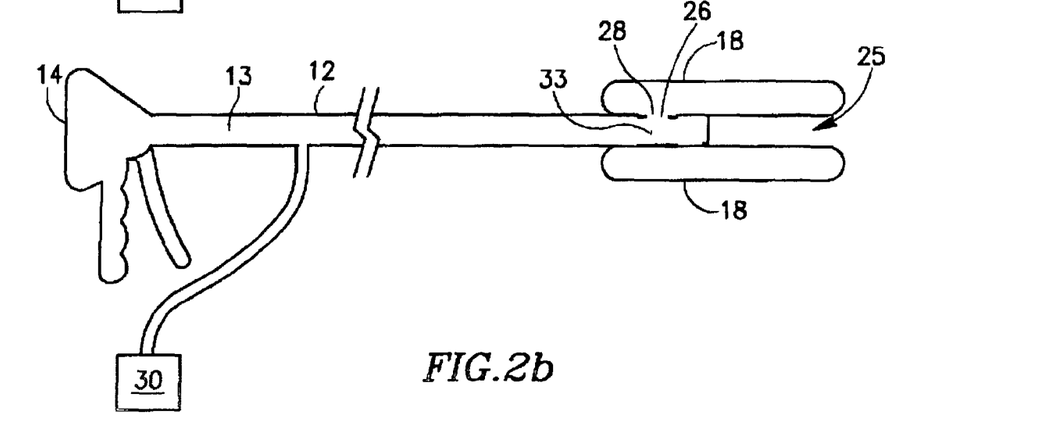
Figure 3A:
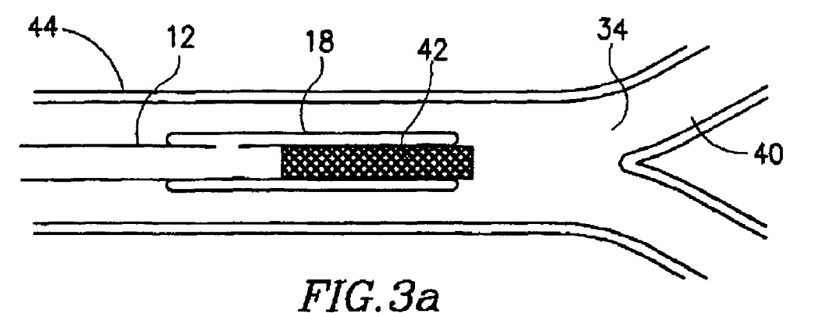
FIG. 3 shows use of the system of FIG. 1 to deliver an object in a body passageway.
Figure 3B:
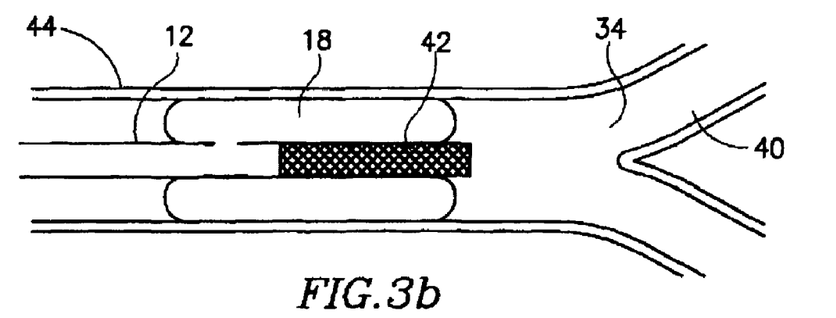
Figure 3C:
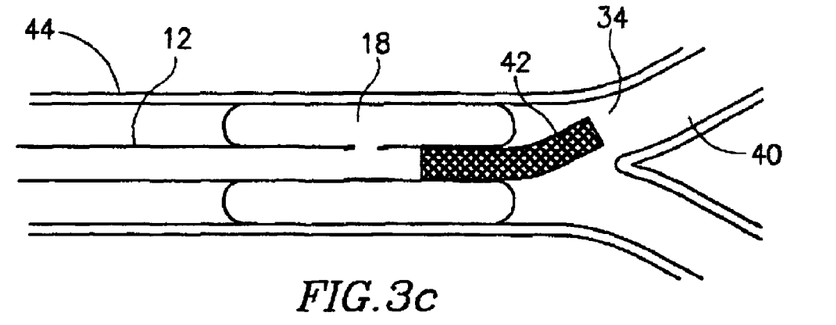
Figure 3D:
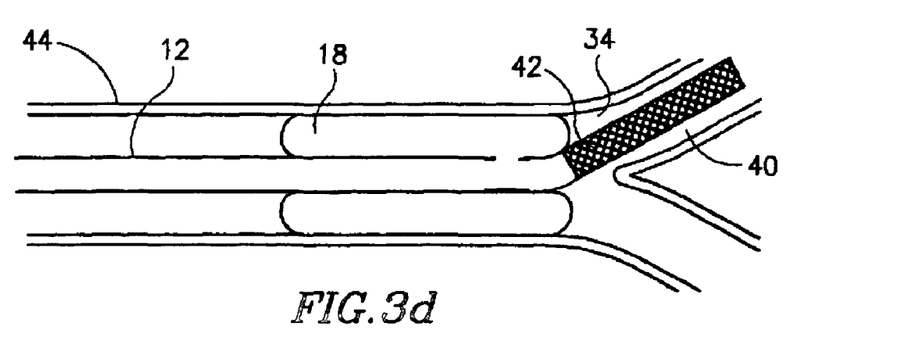

FIG. 2 shows the catheter after inflation of the balloon 18. The balloon 18 surrounds a central passageway 25 which is at least partially occupied by the catheter shaft 12. Since the wall of the balloon is bonded to the catheter shaft only at the seam 32, the balloon can travel along the shaft between a first position shown in FIG. 2a in which it extends maximally in a posterior direction, and a second position shown in FIG. 2b in which it extends maximally in an anterior direction. Movement of the balloon between the positions shown in FIG. 2 occurs by the balloon 18 rolling along the shaft 12 without slipping, with the outer surface 21 of the balloon 18 passing over the inner surface 20.

Figure 9:
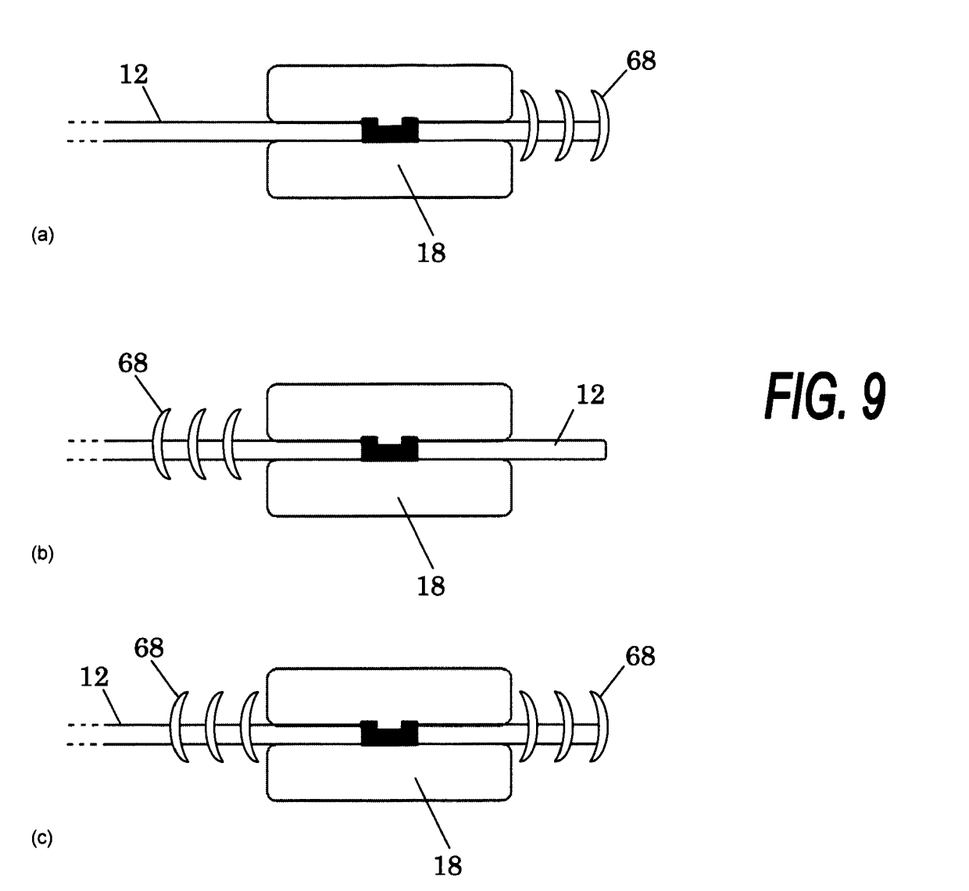
FIG. 9 illustrates three different configurations for the location of retention elements on the catheter shaft in relation to the position of the balloon: (a) distal to the balloon; (b) proximal to the balloon; (c) both distal and proximal to the balloon.

In one embodiment of the system of the present invention, the balloon 18 may be attached to the catheter shaft close to the distal end of catheter shaft 12, such that when said the balloon is caused to roll over said shaft in a distal direction, said balloon may occupy an extreme distal position, such that at least a portion thereof extends beyond the distal tip of said catheter shaft. In a more preferred embodiment, however, balloon 18 is attached to the shaft at a location such that upon rolling, no portion of said balloon ever extends beyond the distal tip of catheter shaft 12. In other words, in this more preferred embodiment, the balloon and catheter are mutually arranged such that a length of catheter shaft always extends beyond the distal margin of said balloon. This arrangement is particularly preferred in cases wherein the presently-disclosed and claimed system is intended for insertion into the vasculature of the subject being treated by means of an "over the wire" method. Furthermore, with certain balloon materials and geometries, the terminal balloon location depicted in FIG. 1 may result in collapse of the portion of the balloon that extends beyond the distal tip of the catheter, thereby releasing any objects, debris or other substances or entities held by that region of the balloon. Consequently, the presently described more preferred embodiment (having the balloon located in a more central position) would be the embodiment of choice for such balloon geometries and materials. The balloon position in this more preferred embodiment is schematically shown in FIGS. 7 and 9.

As mentioned hereinabove, the catheter system of the present invention may, in one mode of operation, be used to retrieve atheromatous plaque debris and other particulate, solid or semi-solid matter present in pathologically-involved blood vessels, and to remove said matter from the body. Furthermore, in a modification of this mode of operation (as will be described hereinbelow), the catheter system of the present invention may also be used to distend and/or expand a pathologically-involved region of a blood vessel wall (e.g. in a region of the internal vessel wall in which there has been a build up of atheromatous plaque), in addition to safely retrieving any plaque debris released by this process. Such debris (and, indeed, any other particulate or semi-solid matter present in the region of the catheter balloon) is retrieved by means of 'trapping' said debris in the space between the balloon wall and the catheter shaft. In the case of debris trapped beneath the distal portion of the balloon, said debris is held in position during proximal movement of the catheter by a syringe-like suction effect (i.e. the creation of a reduced pressure zone within the blood vessel on the distal side of the proximally-moving inflated balloon). Conversely, in the case of debris trapped beneath the proximal portion of the balloon, said debris is held in position during movement of the catheter by the distally-directed hydrodynamic forces exerted by the arterial blood flow. Regardless of which end of the balloon has trapped the debris, the entrapment process is completed following deflation of the balloon (or other expandable element), as a result of which the debris is securely held between the balloon and catheter shaft, thus allowing the safe withdrawal of the catheter system through the vasculature and the removal of said system from the body.

Figure 8:
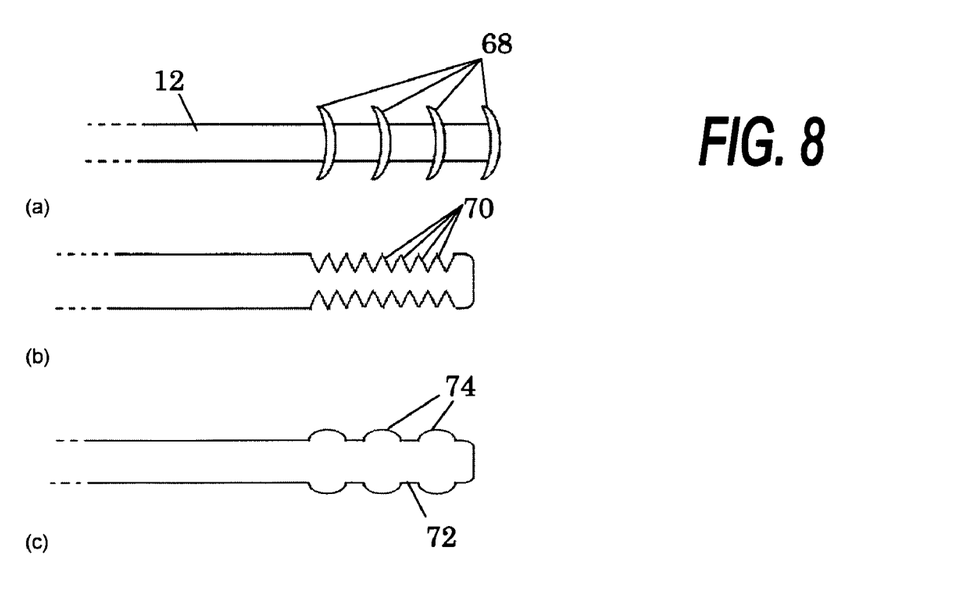
FIG. 8 depicts three different types of retention elements that may be incorporated into the catheter shaft: (a) collection cups; (b) grooves; (c) protrusions.

In another particularly preferred embodiment of the system of the present invention, the catheter shaft further comprises surface features that may assist in the retention of atherosclerotic plaque debris and other solid, semi-solid particulate or aggregate material on the surface of said shaft. By the means of these retention elements, the debris which is trapped in the annular space between the inflated balloon and the catheter shaft may be retained and subsequently removed from the body upon withdrawal of the catheter. FIG. 8 depicts three possible, but not limiting conformations for the retention elements. Firstly (FIG. 8a), the elements may be in the form of collection cups 68 that encircle the catheter shaft. By these means, any debris trapped by the balloon may be retained by the concave inner surface of said cups, even after the balloon has been rolled away from the region of the catheter shaft containing the cups and/or deflated. In an alternative embodiment, shown in FIG. 8b, the retention element is provided in the form of a series of grooves 70, of any shape and profile, radial or axial to the catheter shaft or forming any angle with the catheter shaft. Alternatively, as depicted in FIG. 8c, the retention element is present in the form of a series of surface protrusions arranged such that there is a debris-retaining annular groove or depression 72 between each adjacent pair of protrusions 74, of any shape and profile, radial or axial to the catheter shaft or forming any angle with the catheter shaft. Alternatively, the retention elements may be formed of any combination of the aforementioned grooves and protrusions. The aforementioned retention elements may be located on the catheter shaft 12 surface either on the distal side of the balloon 18 (FIG. 9a), on the proximal side of said balloon (FIG. 9b) or on both sides thereof (FIG. 9c). The three aforementioned examples of retention elements should not, however, be considered as limiting. Rather, any suitable element that may be conveniently formed within the wall of the catheter shaft, or added thereto may be employed in order to increase the retention of debris by the presently-claimed catheter system.

In a further particularly preferred embodiment of the present invention, the presently-disclosed and claimed system further comprises a retaining sleeve for assisting in the collection of debris (and other particulate matter, as mentioned hereinabove) and for the storage thereof prior to, and during, the removal of the catheter from the body. Said debris is collected and stored in the space between the sleeve and a portion of the catheter shaft not occupied by the balloon. In this way, said sleeve functions as an 'extension' of the balloon with respect to its debris-trapping capability. In addition (or alternatively) the debris may be trapped and stored between at least one portion of the sleeve and the balloon. The sleeve, which is attached to the outer surface of the balloon, can—in one embodiment—cover only part of the length of said balloon. Alternatively, the sleeve may be of the same length as the balloon and arranged such that it precisely overlays and covers said balloon. In a further variant, the sleeve may be longer than the length of the balloon and arranged such that the balloon is completely covered thereby. The sleeve may be attached to the balloon at one or more discrete attachment points, at any location on the outer surface of the balloon, such that an annular space exists between said sleeve and the catheter shaft on at least one side of said attachment points. Additionally, or optionally, a similar annular space may also exist between said sleeve and the outer surface of the balloon on at least one side of said sleeve attachment points. The sleeve may be attached to the balloon at one or more discrete attachment points, at any location on the sleeve surface.

Figure 10:
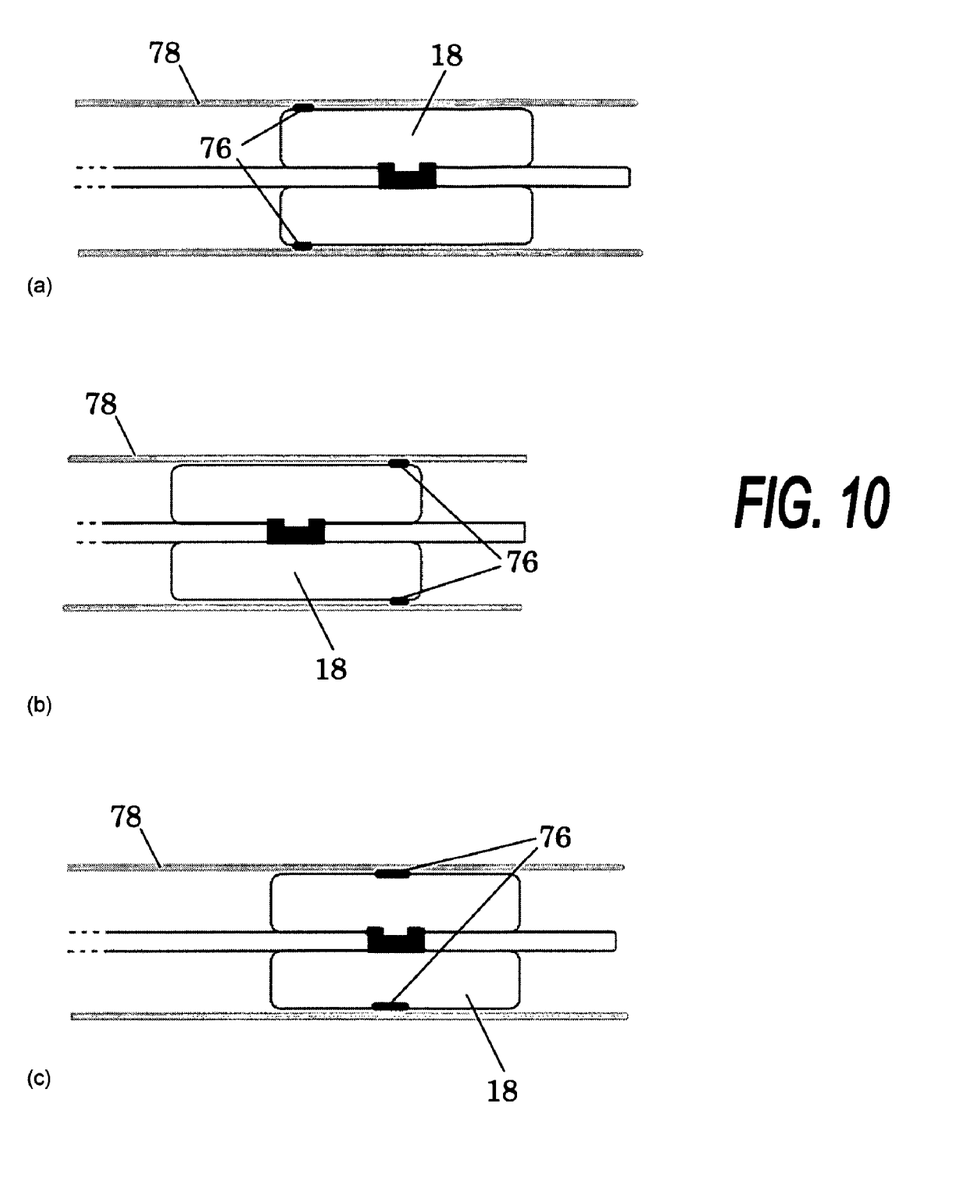
FIG. 10 shows three possibilities for the attachment of the retentive sleeve to the balloon: (a) proximal end attachment; (b) distal end attachment; (c) mid-point attachment.

The attachment points 76 of the sleeve 78 may, as illustrated in FIG. 10, be situated close to the proximal end of the balloon 18 (FIG. 10a), close to the distal end of said balloon (FIG. 10b) or at or close to the mid-point thereof (10c). In addition to the attachment of one end of the sleeve to the balloon, the other end may optionally be attached to the shaft, distal to the balloon or proximal to the balloon, by mean of at least one sleeve extension, or additional fixing feature including, but not limited to, a hook or a basket, in any suitable form, made of any material, metal or polymer or other. Regardless of which specific attachment mean is used, the bonding of the attachment mean to the catheter shaft may be achieved by the use of any suitable biocompatible adhesive, heat welding, ultrasonic welding, or mechanical means. The sleeve may be provided in any suitable form, including (but not limited to) cylindrical, semi-cylindrical, conical, frusto-conical, web-like etc. Said sleeve may be constructed from any suitable biocompatible metal, polymer, other organic material, or of other materials, providing they have the appropriate biomechanical properties. Examples of suitable polymers include those polymers described hereinabove for use in the manufacture of the balloon.

FIG. 3 shows insertion of the catheter tip into a small blood vessel 40, for example, to deliver an object 42 into the vessel 40. The object 42 may be, for example, a stent, as shown in FIG. 3. As another example, the object 42 may be a work tool that is to be delivered to be delivered to a site in the body. The work tool may be, for example, a tool for working on a stenosis, such as a drill, dagger, probe, a radioactive source for brachytherapy, etc. The tool may also be, for example, a light guide, a light source, a radio frequency electrode, or an ultrasound probe. Prior to insertion of the catheter into the body, the object 42 is mounted onto the distal end of the catheter. In FIG. 3a, the catheter tip has been delivered through an artery 44 to the orifice 34 of the vessel 40 with the balloon 18 in its deflated state. The balloon 18 is then inflated so that the inflated balloon is still in its first, proximally located position in which the distal end of the balloon 18 is adjacent to the distal end of the catheter shaft 12, as shown in FIG. 3b. The inflated balloon 18 presses upon the wall of the vessel 44. As shown in FIG. 3c, the catheter tip is then advanced distally into the narrow vessel 40. As the catheter tip advances in the vessel 44, the balloon 18 also advances in the vessel 44. The balloon 18 thus rolls along the shaft and along the wall of the vessel 44. The speed of the balloon 18 in the vessel 44 is about half of that of the tip of the shaft. Since the balloon 18 advances in the vessel 44 at a slower rate than the catheter shaft 12, the balloon 18 moves posteriorly along the shaft 12 towards the second position of the balloon 18 on the shaft, as shown in FIG. 3c. Further anterior advancement of the catheter tip in the vessel 40 causes the balloon to travel further along the shaft posteriorly, until the catheter tip bearing the stent is completely extended beyond the balloon and the stent is positioned in the vessel 40. Since there is a high level of friction between the outer surface of the balloon with the wall of the vessel, there is no slipping of the outer surface of the balloon on the vessel wall, and there is thus no damage to the vessel wall. If the object is a stent, the stent can then be deployed in the vessel 40 by any mechanism (not shown) known in the art for deploying a stent. After deployment of the stent, the balloon 18 may be deflated and the catheter withdrawn from the body.

Figure 11A:
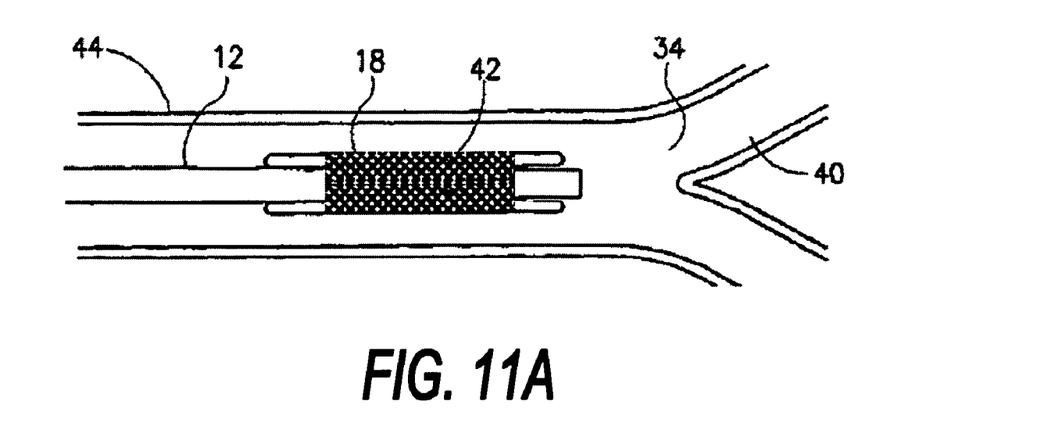
FIG. 11A shows the catheter system with the balloon and stent both in the unexpanded state.
Figure 11B:
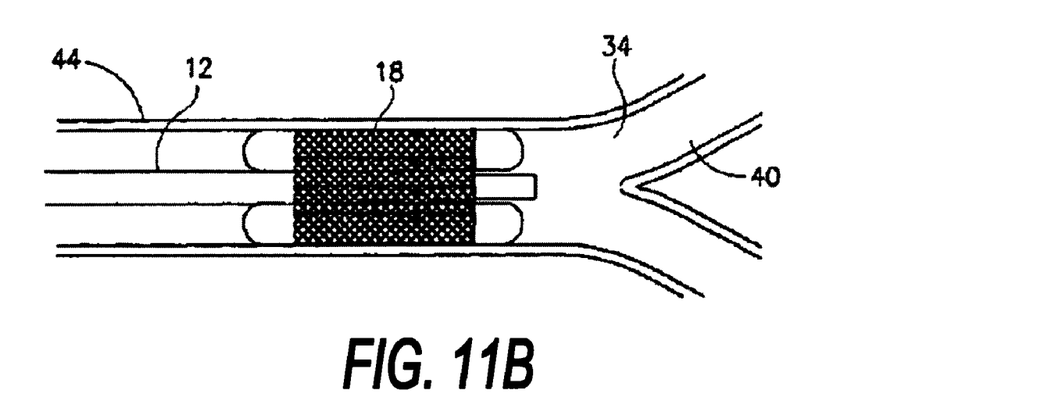
FIG. 11B depicts the system following expansion of both the balloon and stent.
Figure 11C:
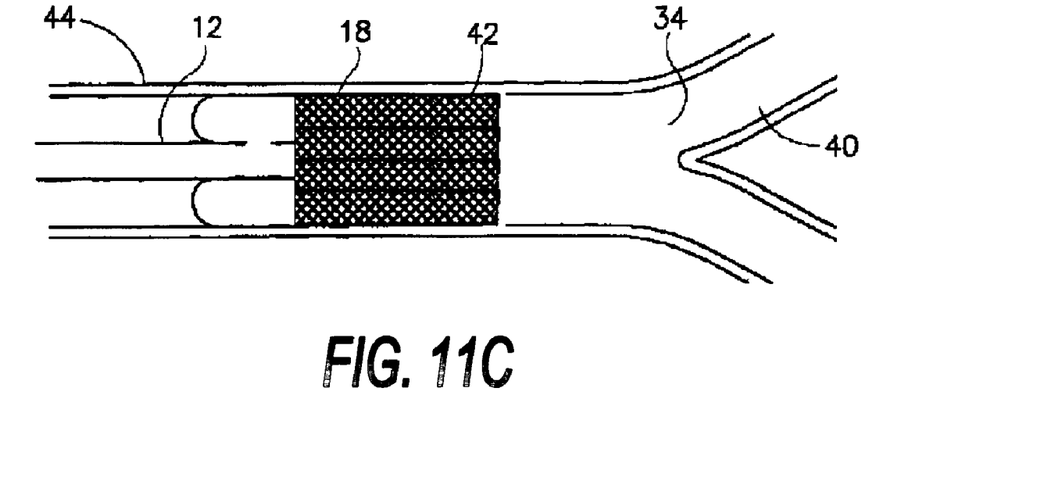
FIG. 11C illustrates the same system after the catheter has been moved a short distance proximally and the balloon has rolled distally over the catheter.

FIG. 11A illustrates a further preferred embodiment of the present invention in which an expandable stent 42 is mounted over the deflated balloon 18 prior to delivery of the catheter system to the treatment site. This embodiment is of particular value in clinical situations in which it is desired that a single catheter system be used to cause both dilation of a pathologically-involved section of a blood vessel (such as a coronary artery) and to safely retrieve any debris released as a result of the dilatation process (or present in the treated region for any other reason). The same embodiment is shown in FIG. 11B following inflation of the balloon 18 and expansion of the stent 42, after which processes both the stent and the regions of the balloon not covered by the stent are in contact with the internal surface of the wall of the blood vessel 44. At this stage, the balloon is disposed such that it may be caused to roll along the blood vessel wall (as described hereinabove) thereby trapping debris released during the stenting process between itself and the catheter shaft 12. One example of this movement of the balloon is shown in FIG. 11C, where the balloon 18 is shown after the catheter shaft 12 has been moved a short distance proximally and the balloon 18 has rolled distally (in relation to said catheter shaft). Alternatively, the balloon may, of course, be caused to roll proximally or, in another preferred mode, it may be caused to alternate between proximal and distal rolling movements, thereby maximizing the debris collection and entrapment. The balloon in this embodiment may also be fitted with a retaining sleeve, as described hereinabove. In addition or in the alternative, the catheter shaft used in this embodiment may also be fitted with retentive surface features as described hereinbefore.

Figure 4:
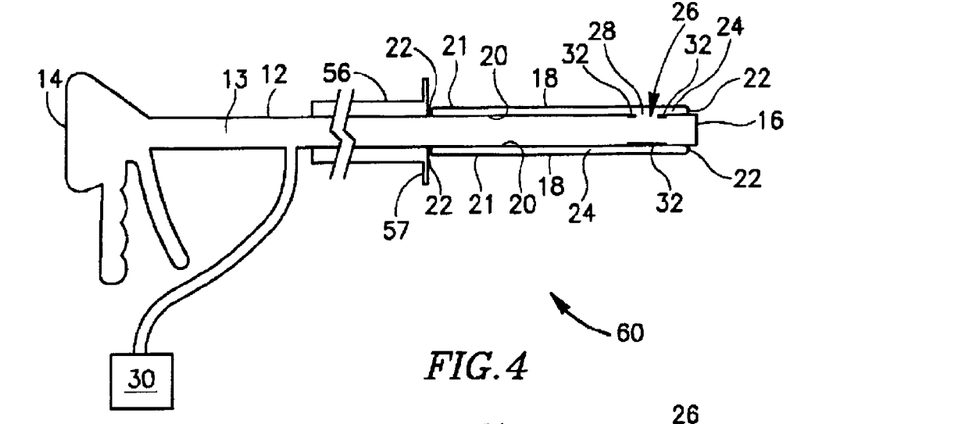
FIG. 4 shows a system in accordance with another embodiment of the invention in which the catheter has a ramming mechanism.
Figure 5A:
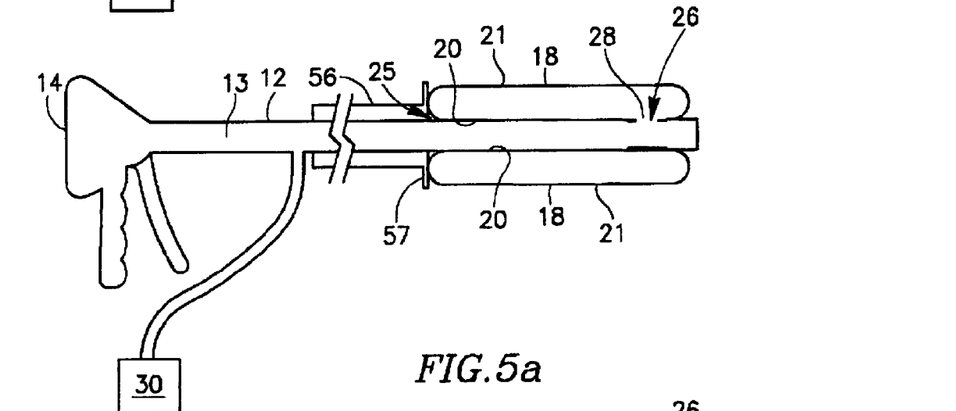
FIG. 5 shows the system of FIG. 4 after inflation of the balloon.
Figure 5B:
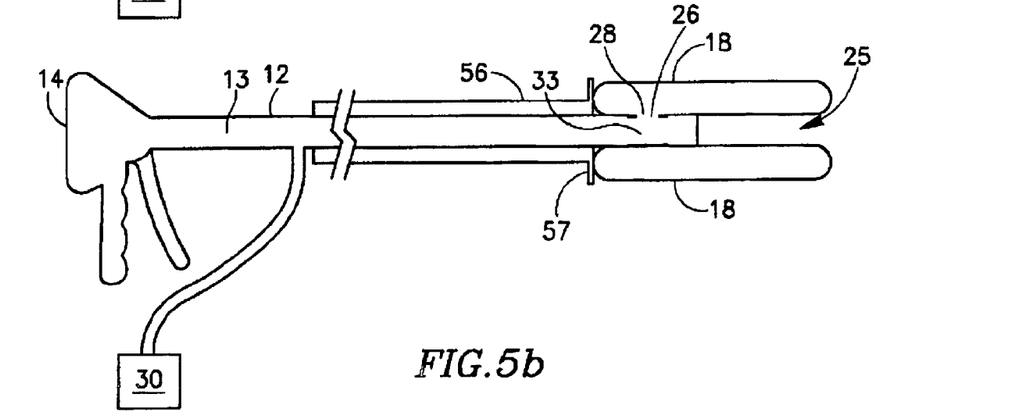
Figure 6A:
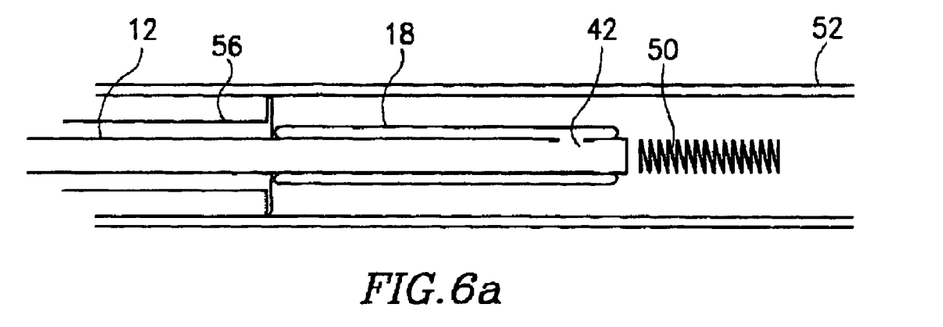
FIG. 6 shows use of the catheter of FIG. 4 to retrieve an object from a body site.
Figure 6B:
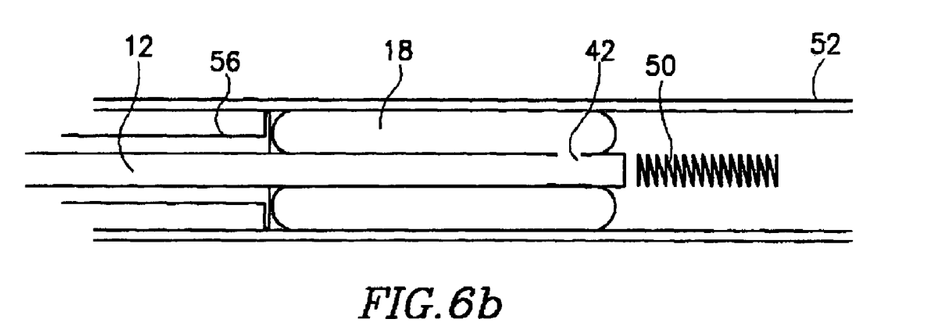
Figure 6C:
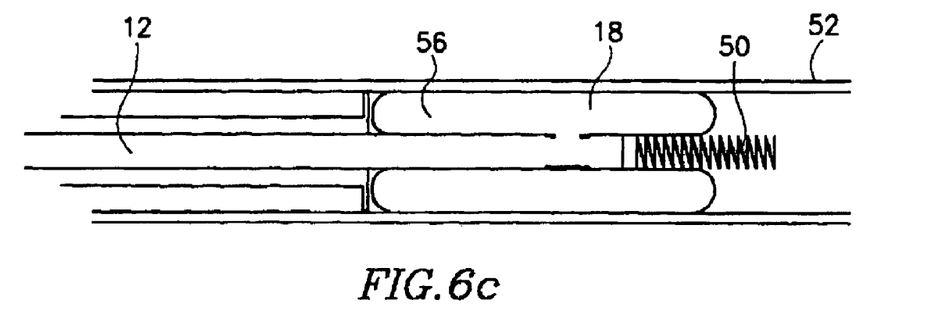
Figure 6D:
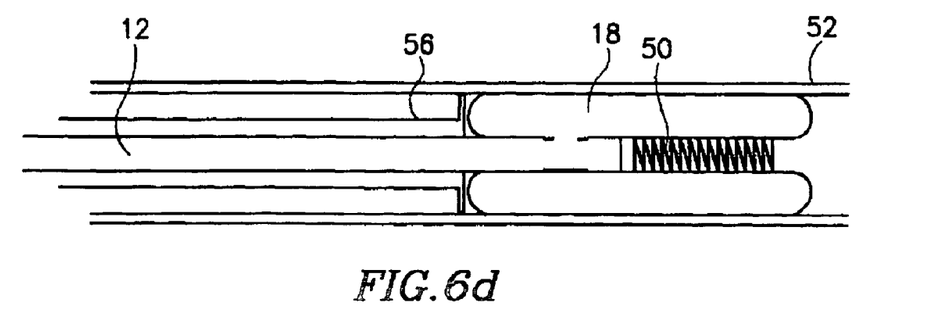

FIG. 4 shows a catheter 60 in accordance with another embodiment of the invention. The catheter 60 has several components in common with the catheter 10 of FIGS. 1 and 2, and similar components in the catheters 10 and 60 are indicated by the same reference numerals, without further comment or explanation. The catheter 60 includes a ramming mechanism that is used to urge the balloon from its first position shown in FIG. 5a to its second position shown in FIG. 5b. The ramming mechanism includes a cylindrical flexible cover 56 enclosing at least a portion of the catheter shaft 12. The distal end of the flexible cover 56 is attached to an annular ramming plate 57. The cover 56 and the ramming plate 57 are slidable along the catheter shaft 12. With the balloon 18 in its first position shown in FIG. 5a, the proximal end of the cover 56 is grasped and pushed distally over the shaft causing the inflated balloon 18 to move from its first position to its second position shown in FIG. 5b

FIG. 6 shows use of the catheter 10 for retrieving an object 50 from a body passageway 52. The object 50 may be, for example, a stent that is to be removed from the body. As another example, the object 50 may be unwanted debris that is to be removed from the body. As shown in FIG. 6a, the tip of the catheter shaft 12 is advanced in the passageway 52 with the balloon 18 in its deflated state in its first position, until the catheter tip is close to the object 50, with the balloon in its deflated state. The balloon 18 is then inflated (FIG. 6b) while remaining in its first position in which the distal end of the balloon 18 is adjacent to the distal end of the catheter tip. The balloon 18 is then urged into its second position by means of the ramming mechanism, as explained above (FIG. 6c). As the balloon 18 rolls distally over the catheter tip, the object 50 enters the lumen 54 of the balloon 18, and is grasped by the balloon 18 (FIG. 6c). The balloon 18 continues to roll over the catheter tip until it has completely enveloped the object 50 as shown in FIG. 6d. The balloon 18 can then be deflated and the catheter removed from the body together with the object 50.

In addition to the modes of use described hereinabove, the present invention may also be used to perform a retrograde ballooning procedure for the combined purpose of removing atheromatous plaque materials and preventing the iatrogenic release of said materials into the blood streams, as will be presently described. By way of introduction, it is to be noted that angioplasty is performed by bringing a balloon catheter to the desired operating site, inflating the balloon to a sufficient pressure to allow distension of the arterial wall, thereby expanding and opening the previously blocked or partially-blocked arterial lumen. Such a procedure, however, may be not well adapted to certain pathological situations. For example, vulnerable plaques may present with a very thin cap, prone to rupture thereby releasing their lipid core and atheromatous material downstream into the blood flow. This, in many cases may lead to subsequent distal embolization and thrombosis. Moreover, stenting of such plaques may induce prolapse of the lipid core and atheromatous materials through the stent mesh, increasing morbidity and mortality by embolization and thrombosis.

The catheter system of the present invention, however, permits the use of a new therapeutic modality, in which the operator introduces the non-inflated balloon distal to the lesion to be treated. The balloon is then inflated and caused to move proximally with its retrograde, rolling, tank track-like motion by gently pulling the catheter shaft in a proximal direction. In this therapeutic modality, the arterial lesion may be squeezed up to its proximal shoulder, allowing release of the lipid core and of the atheromateous material into the blood stream, proximal to the inflated balloon. In the final stage of the procedure, the operator gently pushes the catheter shaft (i.e. in a distal direction), causing a forward, rolling, tank track-like motion of the balloon along the catheter shaft causing the debris and atheromateous material to be trapped between the catheter shaft and the balloon (or—if present—between the retaining sleeve and balloon or within shaft retention elements, as described hereinabove). The operator then deflates the balloon, ensuring complete entrapment of the collected material. The method described hereinabove may also be applied in the opposite direction, i.e. the balloon is inflated on the proximal side of the lesion and then rolled distally. Thus, the use of the system of the present invention in the manner presently described, results in the maximal collection of debris combined with minimal risk of distal embolization.

The invention claimed is:

1. A method for retrieving an object from a body site comprising:
   (a) delivering a catheter to the body site, said catheter comprising:
      (aa) a shaft,
      (ab) an expandable element, the expandable element having an expanded state and having in the expanded state an annular shape surrounding a passageway, wherein the catheter and expandable element are configured so that the expandable element in the expanded state is rollable along at least a portion of the shaft without slipping when a portion of the shaft is positioned in the passageway, and wherein the expandable element is attached to the catheter shaft such that said shaft at all times extends beyond the distal margins of said expandable element;
(b) bringing the expanded element into the expanded state;
(c) rolling the expandable element in the expanded state along said shaft so as to roll over the object to trap said object in an annular space defined between the wall of said expandable element and said shaft of said catheter; and
(d) removing the catheter from the body.

2. A method for removing debris and/or other particulate matter from a blood vessel comprising:
(a) delivering a catheter system via the peripheral vasculature to a pathologically-involved region of said blood vessel, wherein said catheter system comprises:
(i) a shaft
(ii) an expandable element, the expandable element having an expanded state and having in the expanded state an annular shape surrounding a passageway, wherein the catheter and expandable element are configured so that the expandable element in the expanded state is rollable along at least a portion of the shaft without slipping when a portion of the shaft is positioned in the passageway, and wherein the expandable element is attached to the catheter shaft such that said shaft at all times extends beyond the distal margins of said expandable element;
(b) bringing the expandable element into the expanded state,
(c) rolling the expandable element in the expanded state posteriorly or anteriorly or both posteriorly and anteriorly so as to roll over the object thereby entrapping said debris and/or other particulate matter within an annular space formed between said expandable element and said shaft;
(d) deflating said expandable element, thereby entrapping said debris and/or other particulate matter between the deflated expandable element and the catheter shaft; and
(e) removing the catheter system together with the entrapped debris and/or other particulate matter from the body by means of withdrawing said catheter system through the vasculature.

3. The method according to claim 1 wherein the catheter shaft further comprises retention elements on its external surface.

4. The method according to claim 2 wherein the catheter shaft further comprises retention elements on its external surface.

5. The method according to claim 1, wherein the catheter system further comprises a retaining sleeve, wherein the inner surface of the wall of said sleeve is attached at one or more attachment points to the surface of the expandable element, such that an annular space exists between said sleeve and the catheter shaft on at least one side of said attachment points, and where at least part of the entrapped debris and/or particulate matter is entrapped within said annular space.

6. The method according to claim 2, wherein the catheter system further comprises a retaining sleeve, wherein the inner surface of the wall of said sleeve is attached at one or more attachment points to the surface of the expandable element, such that an annular space exists between said sleeve and the catheter shaft on at least one side of said attachment points, and where at least part of the entrapped debris and/or particulate matter is entrapped within said annular space.

7. The method according to claim 1, wherein the expandable element is a balloon.

8. The method according to claim 2, wherein the expandable element is a balloon.

9. The method according to claim 1 wherein said catheter further includes a ramming mechanism capable of sliding along said shaft for rolling said expandable element anteriorly on said shaft and wherein said step (c) comprises rolling said expandable element in the expanded state anteriorly along said shaft by ramming said expandable element with said ramming mechanism.

10. The method according to claim 1 wherein said rolling of step (c) is selected from,
rolling said expandable element anteriorly along said shaft,
rolling said expandable element posteriorly along said shaft, and
rolling said expandable element anteriorly and posteriorly along said shaft.

11. The method according to claim 7 further including the step of deflating said balloon prior to said step of removing said catheter.

12. The method according to claim 2 wherein said catheter further includes a ramming mechanism capable of sliding along said shaft for rolling said expandable element anteriorly on said shaft and wherein said step (c) comprises rolling said expandable element in the expanded state anteriorly along said shaft by ramming said expandable element with said ramming mechanism.

* * * * *